United States Patent
Faryniarz et al.

(10) Patent No.: US 7,404,949 B2
(45) Date of Patent: *Jul. 29, 2008

(54) METHODS AND COMPOSITIONS USEFUL TO PREVENT IN-GROWN HAIR ARISING FROM SHAVING

(75) Inventors: Joseph Raymond Faryniarz, Middlebury, CT (US); Michael Charles Cheney, Trumbull, CT (US); Anthony William Johnson, Fairfield, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 753 days.

This patent is subject to a terminal disclaimer.

(21) Appl. No.: 10/800,810

(22) Filed: Mar. 15, 2004

(65) Prior Publication Data

US 2005/0202054 A1   Sep. 15, 2005

(51) Int. Cl.
*A61Q 9/02* (2006.01)

(52) U.S. Cl. .................. 424/73; 514/886; 514/887; 514/557

(58) Field of Classification Search .................. 424/73, 424/401
See application file for complete search history.

(56) References Cited

U.S. PATENT DOCUMENTS

| | | | |
|---|---|---|---|
| 4,755,472 A | 7/1988 | Ismail et al. | |
| 4,775,530 A | 10/1988 | Perricone | |
| 4,867,967 A | 9/1989 | Crutcher | |
| 4,944,939 A | 7/1990 | Moore | |
| 5,350,694 A * | 9/1994 | Zimmerle | 436/2 |
| 5,578,641 A | 11/1996 | Jackson et al. | |
| 5,641,495 A * | 6/1997 | Jokura et al. | 424/401 |
| 5,643,586 A | 7/1997 | Perricone | |
| 5,962,018 A | 10/1999 | Curtis et al. | |
| 6,001,340 A | 12/1999 | Rosen et al. | |
| 6,007,649 A | 12/1999 | Haas et al. | |
| 6,156,299 A | 12/2000 | Rosen et al. | |
| 6,461,599 B1 | 10/2002 | Ruben | |
| 6,521,237 B2 | 2/2003 | Cole et al. | |
| 6,544,531 B1 | 4/2003 | Cole et al. | |
| 7,067,556 B2 | 6/2006 | Bhagwat et al. | |
| 2003/0017177 A1 | 1/2003 | Perricone | |
| 2003/0095991 A1 | 5/2003 | Cole et al. | |

FOREIGN PATENT DOCUMENTS

| | | |
|---|---|---|
| EP | 0 396 857 | 2/1990 |
| EP | 0 713 093 | 11/1995 |
| EP | 1 090 630 | 3/1999 |
| EP | 1 192 940 | 10/2001 |
| GB | 1039337 | 11/1963 |
| JP | 58/104275 | 12/1981 |
| JP | 07206626 | 8/1995 |
| JP | 10/175844 | 2/1997 |
| WO | 97/33560 | 9/1997 |
| WO | 00/61107 | 10/2000 |
| WO | 03/099250 | 12/2003 |
| WO | 03/099251 | 12/2003 |

OTHER PUBLICATIONS

Flick, E., Cosmetic and Toiletry Formulations, 1996, Noyes Publications, 2nd Ed., vol. 5, pp. 508 and 543.*
Paniccia, P., Poucher's Perfumes, Cosmetics, and Soaps, 2000, Kluwer Academic Publishers, (10$^{th}$ ed. by Hilda Bulter), pp. 348-356.*
International Search Report.

* cited by examiner

*Primary Examiner*—Sreeni Padmanabhan
*Assistant Examiner*—Gina Yu
(74) *Attorney, Agent, or Firm*—Milton L. Honig

(57) ABSTRACT

A method and composition is provided for managing in-grown hair which involves applying to those areas malonic acid or a salt thereof in a carrier. The method and composition allows for comfortable shaving of skin by minimizing the problem of in-grown hair.

4 Claims, No Drawings

METHODS AND COMPOSITIONS USEFUL TO PREVENT IN-GROWN HAIR ARISING FROM SHAVING

BACKGROUND OF THE INVENTION

1. Field of the Invention

The invention concerns shaving and pre-shaving methods and preparations effective on skin having in-grown hairs.

2. The Related Art

Men in many societies are expected to be clean shaven. The process is usually accomplished in the morning, often sleepy-eyed in a ritual removing the unsightly stubble on face and throat. The desired result of a smooth skin surface encounters many obstacles.

The basic process of drawing a blade across a body surface is best done on a perfectly flat template. Of course, every face possesses unique deviations from the perfectly flat. A shave may be close or too close in certain areas and insufficiently close in others. Parameters of elasticity, turgo, smoothness and hair type are further considerations. The art has moved to compensate for these deviations. One approach is optimization of a razor system. The other involves applying pre-shaving compositions to prepare the skin or use of lubricating compositions during the cutting process.

Shaving for black males can be particularly difficult. This group of individuals often possesses facial hair with natural curvature. When hair is sharpened through razor contact it can either penetrate the epidermis in an arc or pierce the follicular wall. Penetration elicits a painful response.

The art has responded to the problem of in-grown hair. U.S. Pat. No. 4,775,530 (Perricone) treats "razor bumps" with alpha-hydroxyacids or derivatives thereof. U.S. Pat. No. 6,156,299 (Rosen et al.) topically applies an acetylsalicylic acid composition to beard areas of the face as an after shave to inhibit growth. U.S. Pat. No. 5,962,018 (Curtis et al.) discloses a method for treating in-grown hair with an anhydrous composition containing a water soluble organic acid encapsulated into hydrophobic microspheres. The organic acid can elute in the presence of water when applied to the skin. Another approach is found in U.S. Pat. No. 6,461,599 (Reuben) disclosing formulating a shaving composition with abrasive particles for aiding in liberation of hairs grown aberrantly. Still another approach is found in U.S. Pat. No. 4,944,939 (Moore) describing a shaving composition incorporating salicylic acid, a glucocorticoid and sulphur.

None of the foregoing approaches to controlling the in-grown hair problem have fully met expectations of those experiencing the problem.

SUMMARY OF THE INVENTION

A method is provided for overcoming in-grown hair including:
  providing a cosmetic composition comprising:
  (i) from about 0.1 to about 30% by weight of malonic acid or a salt thereof; and
  (ii) from about 1 to about 99.9% by weight of a cosmetically acceptable carrier;
  applying the composition to an area of skin having in-grown hair prior to, concurrently with or subsequent to removing hair by razor action from the area with in-grown hair.

DETAILED DESCRIPTION OF THE INVENTION

Now it has been found that the problems associated with in-grown hair can be avoided by applying to parts of the body malonic acid or a salt thereof delivered in a cosmetically acceptable carrier.

Salts of malonic acid may include those having cations such as ammonium, $C_1$-$C_{30}$ ammonium, alkali metal ion, alkaline earth metal ion and combinations thereof. Typical of the $C_1$-$C_{30}$ ammonium cations are triethanolammonium, diethanolammonium, monoethanolammonium, tris(hydroxymethyl)methane ammonium, dimethylethanolammonium, calcium, lithium, potassium, sodium and mixtures thereof. Amino acids may also serve as counterions to the malonate. Representative of this group are arginine, lycine, glycine and tryptophane. Most preferred are the malonate salts with cations generated from dimethylaminoethanol, tris (hydroxymethyl)aminomethane and ammonia.

Amounts of the acid or salt according to the present invention may range from about 0.1 to about 30%, preferably from about 0.5 to about 20%, more preferably from about 1 to about 15%, optimally from about 3 to about 10% by weight of the composition.

Compositions of this invention will also include a cosmetically acceptable carrier. Amounts of the carrier may range from 1 to 99.9%, preferably from about 70 to about 95%, optimally from about 80 to about 90%. Among the useful carriers are water, emollients, fatty acids, fatty alcohols, humectants, thickeners and combinations thereof. The carrier may be aqueous, anhydrous or an emulsion. Preferably the compositions are aqueous, especially water and oil emulsions of the W/O or O/W or W/O/W triplex variety. Water when present may be in amounts ranging from about 5 to about 95%, preferably from about 20 to about 70%, optimally from about 35 to about 60% by weight.

Emollient materials may serve as cosmetically acceptable carriers. These may be in the form of silicone oils, synthetic esters and hydrocarbons.

Amounts of the emollients may range anywhere from about 0.1 to about 95%, preferably between about 1 and about 50% by weight.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to $0.1$ m$^2$/s at 25 C. Among the preferred nonvolatile emollients useful in the present compositions are the polydimethyl siloxanes having viscosities from about $1 \times 10^5$ to about $4 \times 10^4$ m$^2$/s at 25 C.

Another class of nonvolatile silicones are emulsifying and non-emulsifying silicone elastomers. Representative of this category is DimethiconeNinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:
(1) Alkenyl or alkyl esters of fatty acids having 10 to 20 carbon atoms. Examples thereof include isoarachidyl neopentanoate, isononyl isononanoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

(4) Wax esters such as beeswax, spermaceti wax and tribehenin wax.

(5) Sterols esters, of which cholesterol fatty acid esters are examples thereof.

(6) Sugar ester of fatty acids such as sucrose polybehenate and sucrose polycottonseedate.

Hydrocarbons which are suitable cosmetically acceptable carriers include petrolatum, mineral oil, $C_{11}$-$C_{13}$ isoparaffins, polyalphaolefins, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, hydroxystearic, oleic, linoleic, ricinoleic, arachidic, behenic and erucic acids.

Fatty alcohols having from 10 to 30 carbon atoms are another useful category of cosmetically acceptable carrier. Illustrative of this category are stearyl alcohol, lauryl alcohol, myristyl alcohol and cetyl alcohol.

Humectants of the polyhydric alcohol-type can be employed as cosmetically acceptable carriers. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition.

Thickeners can be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, and silicates such as magnesium aluminum silicate (Veegum®). Amounts of the thickener may range from 0.0001 to 10%, usually from 0.001 to 1%, optimally from 0.01 to 0.5% by weight.

Cosmetic compositions of the present invention may be in any form. These forms may include lotions, creams, roll-on formulations, sticks, mousses, aerosol and non-aerosol sprays and fabric (e.g. nonwoven textile)-applied formulations.

Surfactants may also be present in cosmetic compositions of the present invention. Total concentration of the surfactant when present may range from about 0.1 to about 40%, preferably from about 1 to about 20%, optimally from about 1 to about 5% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionate, $C_8$-$C_{20}$ alkyl ether phosphates, $C_8$-$C_{20}$ sarcosinates and combinations thereof.

Sunscreen actives may also be included in compositions of the present invention. Particularly preferred are such materials as ethylhexyl p-methoxycinnamate, available as Parsol MCX®, Avobenzene, available as Parsol 1789® and benzophenone-3, also known as Oxybenzone. Inorganic sunscreen actives may be employed such as microfine titanium dioxide, zinc oxide, polyethylene and various other polymers. Amounts of the sunscreen agents when present may generally range from 0.1 to 30%, preferably from 2 to 20%, optimally from 4 to 10% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may include vitamins. Illustrative vitamins are Vitamin A (retinol), Vitamin $B_2$, Vitamin $B_6$, Vitamin C, Vitamin E and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight.

Another type of useful substance can be that of an enzyme such as oxidases, proteases, lipases and combinations. Particularly preferred is superoxide dismutase, commercially available as Biocell SOD from the Brooks Company, USA.

Skin lightening compounds may be included in the compositions of the invention. Illustrative substances are placental extract, lactic acid, niacinamide, arbutin, kojic acid, ferulic acid, resorcinol and derivatives including 4substituted resorcinols and combinations thereof. Amounts of these agents may range from about 0.1 to about 10%, preferably from about 0.5 to about 2% by weight of the compositions.

A variety of herbal extracts may optionally be included in compositions of this invention. Illustrative are green tea, chamomile, licorice and extract combinations thereof. The extracts may either be water soluble or water-insoluble carried in a solvent which respectively is hydrophilic or hydrophobic. Water and ethanol are the preferred extract solvents.

Also included may be such materials as lipoic acid, retinoxytrimethylsilane (available from Clariant Corp. under the Silcare 1M-75 trademark), ceramides (including Ceramide 1, Ceramide 3, Ceramide 3B and Ceramide 6), dehydroepiandrosterone (DHEA) and combinations thereof. Amounts of these materials may range from about 0.000001 to about 10%, preferably from about 0.0001 to about 1% by weight.

Colorants, fragrances, opacifiers and abrasives may also be included in compositions of the present invention. Each of these substances may range from about 0.05 to about 5%, preferably between 0.1 and 3% by weight.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLE 1

Subsequent to shaving, a post-application formula is placed onto areas of the face that have already been shaved. The formula is outlined in Table I below.

TABLE I

| INGREDIENT | WEIGHT % |
|---|---|
| PHASE A | |
| Water | Balance |
| Disodium EDTA | 0.05 |
| Methyl Paraben | 0.15 |
| Magnesium Aluminum Silicate | 0.60 |
| Triethanolamine | 1.20 |
| PHASE B | |
| Xanthan Gum | 0.20 |
| Natrosol ® 250HHR (ethyl cellulose) | 0.50 |
| Butylene Glycol | 3.00 |
| Glycerin | 2.00 |
| PHASE C | |
| Sodium Stearoyl Lactylate | 0.10 |
| Glycerol Monostearate | 1.50 |
| Stearyl Alcohol | 1.50 |

TABLE I-continued

| INGREDIENT | WEIGHT % |
|---|---|
| Isostearyl Palmitate | 3.00 |
| Silicone Fluid | 1.00 |
| Cholesterol | 0.25 |
| Sorbitan Stearate | 1.00 |
| Butylated Hydroxy Toluene | 0.05 |
| Vitamin E Acetate | 0.01 |
| PEG-100 Stearate | 2.00 |
| Stearic Acid | 3.00 |
| Propyl Paraben | 0.10 |
| Parsol MCX ® | 2.00 |
| Caprylic/Capric Triglyceride | 0.50 |
| Hdroxycaprylic Acid | 0.01 |
| C12-15 Alkyl Octanoate | 3.00 |
| PHASE D | |
| Tris(hydroxymethyl)aminomethane Salt of Malonic Acid | 2.00 |
| PHASE E | |
| Vitamin A Palmitate | 0.10 |
| Bisabolol | 0.01 |
| Vitamin A Acetate | 0.01 |
| Fragrance | 0.03 |
| Retinol 50C | 0.02 |

EXAMPLE 2

Illustrated herein is a skin cream pre-shaving formulation according to the present invention.

TABLE II

| INGREDIENT | WEIGHT % |
|---|---|
| Glycerin | 6.93 |
| Niacinamide | 5.00 |
| Dimethylaminoethanol Salt of Malonic Acid | 5.00 |
| Permethyl 101A[1] | 3.00 |
| Sepigel 305[2] | 2.50 |
| Q2-1403[3] | 2.00 |
| Isopropyl Isostearate | 1.33 |
| Arlatone 2121[4] | 1.00 |
| Cetyl Alcohol CO-1695 | 0.72 |
| SEFA Cottonate[5] | 0.67 |
| Tocopherol Acetate | 0.50 |
| Panthenol | 0.50 |
| Stearyl Alcohol | 0.48 |
| Titanium Dioxide | 0.40 |
| Disodium EDTA | 0.10 |
| Glydant Plus[6] | 0.10 |
| PEG-100 Stearate | 0.10 |
| Stearic Acid | 0.10 |
| Purified Water | Balance |

[1]Isohexadecane, Presperse Inc., South Plainfield, NJ
[2]Polyacrylamide(and)C13-14 Isoparaffin(and) Laureth-7, Seppic Corporation, Fairfield, NJ
[3]dimethicone(and)dimethiconol, Dow Corning Corp. Midland, MI
[4]Sorbitan Monostearate and Sucrococoate, ICI Americas Inc., Wilmington, DE
[5]Sucrose ester of fatty acid
[6]DMDM Hydantoin (and) Iodopropynyl Butylcarbamate, Lonza Inc., Fairlawn, NJ

EXAMPLE 3

Illustrative of a powdered post-shaving composition according to the present invention outlined in Table III below.

TABLE III

| INGREDIENT | WEIGHT % |
| --- | --- |
| Polysilicone-11 | 22.5 |
| Cyclomethicone | 54 |
| Petrolatum | 11 |
| Ammonium Malonate (50% in water) | 7 |
| Dimethicone Copolyol | 0.5 |

EXAMPLE 4

A relatively anhydrous composition according to the present invention for application prior to shaving is reported in Table IV below.

TABLE IV

| INGREDIENT | WEIGHT % |
| --- | --- |
| Cyclomethicone | 80.65 |
| Dimethicone | 9.60 |
| Squalane | 6.00 |
| Isostearic Acid | 1.90 |
| Borage Seed Oil | 0.90 |
| Sodium Malonate | 0.50 |
| Retinyl Palmitate | 0.25 |
| Ceramide 6 | 0.10 |
| Tocopherol | 0.10 |

EXAMPLE 5

An aerosol packaged foaming shaving preparation applied for concurrent use with a razor is outlined in Table V.

TABLE V

| INGREDIENT | WEIGHT % |
| --- | --- |
| Sunflower Seed Oil | 20.00 |
| Maleated Soybean Oil | 5.00 |
| Silicone Urethane | 1.00 |
| Polyglycero-4 Oleate | 1.00 |
| Sodium Stearate | 15.00 |
| Sodium Lauryl Ether Sulphate (25% active) | 15.00 |
| Cocoamidopropylbetaine | 15.00 |
| DC 1784 ® (Silicone Emulsion 50%) | 5.00 |
| Polyquaternium-11 | 1.00 |
| Triethanolammonium Malonate | 1.00 |
| Water | Balance |

EXAMPLE 6

A clinical study was undertaken to evaluate the efficacy of a variety of malonates in comparison to a salicylate salt utilized commercially as a razor-bump active.

The protocol was a simple monadic test. Each respondent tested only a single product. These were given to the panelists to use once daily, regardless of whether they had shaved that day or not. They were also instructed not to share the product with anyone else, as the amount in the pack was measured for use by one person only. All formulas were packed in plain colored 100 ml bottles fitted with a pump dispenser (designed to dispense the correct amount for each usage occasion, i.e. 1.8 grams). Feedback on efficacy was through use of a questionnaire answered by the panelists. The panelists were dark skinned males age between 18 and 55 years. They were selected on the basis of having suffered razor bumps in the last month, but were not afflicted to such a serious extent that shaving was impossible.

The base formula used for all cells within the test is listed in Table VI.

TABLE VI

| Ingredient | Weight % |
| --- | --- |
| Magnesium Aluminum Silicate | 0.30 |
| Xanthan Gum | 0.10 |
| Active Ingredient* | — |
| Methyl Paraben | 0.14 |
| Disodium EDTA | 0.05 |
| Glycerine | 7.00 |
| Hydroxypropyl Starch Phosphate | 1.50 |
| Glycol Stearate | 1.39 |
| PEG 100 Stearate | 1.19 |
| Glyceryl Monostearate | 0.65 |
| Cetyl Alcohol | 0.37 |
| Stearic Acid | 2.35 |
| White Mineral Oil | 2.25 |
| White Petroleum Jelly | 0.50 |
| Parsol ® MCX/Escalol ® 557 | 0.50 |
| Silicon DC 200/200 | 0.50 |
| Glydant ® (DMDM Hydantoin) | 0.25 |
| Fragrance Oil | 0.01 |
| Licorice Extract | 0.10 |
| Alpha Bisabolol | 0.20 |
| Borage Seed Oil | 0.50 |
| Triethanolamine 99% | 0.33 |
| Deionized Water | balance |

TABLE VII

| Cell | Active | Weight % |
| --- | --- | --- |
| A | Triethanolamine Salt of Salicylic Acid | 2 |
| B | Triethanolamine Salt of Malonic Acid | 5 |
| C | Ammonia Salt of Malonic Acid | 5 |
| D | Tris(hydroxymethyl) Amino Methane Salt of Malonic Acid | 5 |

Four product cells were utilized. The active salts as reported in Table VII were formulated into the base composition as shown in Table VI. Cell A with a formula based based on a salicylate active was utilized as a comparative control. Results of the test are recorded as answers to a questionnaire by the participating panelists. These are recorded in Table VIII.

TABLE VIII

| | CELL A | CELL B | CELL C | CELL D |
| --- | --- | --- | --- | --- |
| Question: Prevents razor burn/itchiness | | | | |
| Panelists | 49 | 53 | 54 | 48 |
| (wt5) Strongly Agree | 63 | 75 | 87 | 77 |
| (wt4) Agree | 29 | 21 | 9 | 15 |
| (wt3) Neither agree nor Disagree | 4 | 2 | 2 | 2 |
| (wt2) Disagree | 4 | 2 | 2 | 6 |
| (wt1) Strongly Disagree | — | — | — | — |
| Mean | 4.51 | 4.7 | 4.81 | 4.63 |
| Standard Deviation | 0.77 | 0.61 | 0.55 | 0.82 |
| Standard Error | 0.11 | 0.08 | 0.08 | 0.12 |
| Error Variance | 0.01 | 0.01 | 0.01 | 0.01 |
| Question: Prevents in-grown hairs forming | | | | |
| Panelists | 49 | 53 | 54 | 48 |
| (wt5) Strongly Agree | 47 | 72 | 67 | 60 |
| (wt4) Agree | 41 | 23 | 22 | 19 |
| (wt3) Neither agree nor Disagree | 6 | — | 7 | 4 |
| (wt2) Disagree | 6 | 6 | 4 | 17 |
| (wt1) Strongly Disagree | — | — | — | — |
| Mean | 4.29 | 4.6 | 4.52 | 4.23 |

TABLE VIII-continued

|  | CELL A | CELL B | CELL C | CELL D |
|---|---|---|---|---|
| Standard Deviation | 0.84 | 0.77 | 0.79 | 1.13 |
| Standard Error | 0.12 | 0.11 | 0.11 | 0.16 |
| Error Variance | 0.01 | 0.01 | 0.01 | 0.03 |
| Question: Clears up my old razor bump scars | | | | |
| Panelists | 49 | 53 | 54 | 48 |
| (wt5) Strongly Agree | 57 | 72 | 85 | 71 |
| (wt4) Agree | 31 | 25 | 13 | 21 |
| (wt3) Neither agree nor Disagree | 6 | — | 2 | 6 |
| (wt2) Disagree | 4 | 4 | — | 2 |
| (wt1) Strongly Disagree | 2 | — | — | — |
| Mean | 4.37 | 4.64 | 4.83 | 4.6 |
| Standard Deviation | 0.93 | 0.68 | 0.42 | 0.71 |
| Standard Error | 0.13 | 0.09 | 0.06 | 0.1 |
| Error Variance | 0.02 | 0.01 | 0 | 0.01 |

Based upon the panelists' comments from use of the different products, it is evident that the malonic acid neutralized actives containing formulas were better than the salicylate control. More specifically, the order of decreasing effectiveness was as follows: ammonia neutralized malonic acid, tris(hydroxymethyl)aminomethane neutralized malonic acid, triethanolamine neutralized malonic acid and triethanolamine neutralized salicylic acid.

Twenty-four (24) female panelists were used for an eight week study. The panelists were randomly assigned to one of two test groups. They were directed to use their test product (in place of any other facial product) twice a day for eight weeks. Panelists were required to attend five evaluation sessions, each of which consisted of facial complexion evaluation, a self-evaluation and a photographic evaluation.

Razor bumps (in-grown hair) effects were one of the properties which were focused upon. The results indicated a 139% improvement in razor bumps reduction utilizing the trisamino salt in place of the commercial ammonium glycolate. The visual assessment revealed much lower razor bumps with the trisamino salt than with the ammonium glycolate.

An aerosol is prepared using 92% by weight of the concentrate in Table VIII and 8% propellant, the latter being a combination of dimethylether, isobutane and propane.

The foregoing description and examples illustrate selected embodiments of the present invention. In light thereof variations and modifications will be suggested to one skilled in the art, all of which are within the spirit and purview of this invention.

What is claimed is:

1. A method for overcoming in-grown hair comprising:
   providing a cosmetic composition comprising:
   (i) from about 0.1 to about 30% by weight of malonic acid or a salt thereof; and
   (ii) from about 1 to about 99.9% by weight of a cosmetically acceptable carrier;
   applying the composition to an area of skin having in-grown hair prior to, concurrently with or subsequent to removing hair by razor action from the area with in-grown hair.

2. The method according to claim 1 wherein the salt is tris(hydroxymethyl)methylammonium malonate.

3. The method according to claim 1 wherein the salt is ammonium malonate.

4. The method according to claim 1 wherein the salt is triethanolarnmonium malonate.

* * * * *